United States Patent [19]
Ajji et al.

[11] Patent Number: 5,864,403
[45] Date of Patent: Jan. 26, 1999

[54] METHOD AND APPARATUS FOR MEASUREMENT OF ABSOLUTE BIAXIAL BIREFRINGENCE IN MONOLAYER AND MULTILAYER FILMS, SHEETS AND SHAPES

[75] Inventors: Abdellah Ajji, Boucherville; Jacques Guèvremont, Montréal, both of Canada

[73] Assignee: National Research Council of Canada, Ottawa, Canada

[21] Appl. No.: 27,561

[22] Filed: Feb. 23, 1998

[51] Int. Cl.$^6$ .................................................. G01J 4/04
[52] U.S. Cl. ............................................. 356/365; 356/367
[58] Field of Search ............................... 356/364, 365, 356/366, 367, 368, 369; 250/225

[56] References Cited

U.S. PATENT DOCUMENTS

| | | | |
|---|---|---|---|
| 3,902,805 | 9/1975 | Redner | 356/367 |
| 4,309,110 | 1/1982 | Tumerman | 356/365 |
| 4,521,111 | 6/1985 | Paulson et al. | 356/367 |
| 4,850,710 | 7/1989 | Mochida et al. | 356/367 |
| 4,909,630 | 3/1990 | Gawrish et al. | 356/364 |
| 4,973,163 | 11/1990 | Sakai et al. | 356/367 |
| 5,257,092 | 10/1993 | Noguchi et al. | 356/367 |
| 5,319,194 | 6/1994 | Yoshizumi et al. | 250/225 |
| 5,406,371 | 4/1995 | Sakai et al. | 356/367 |
| 5,504,581 | 4/1996 | Nagata et al. | 356/364 |

FOREIGN PATENT DOCUMENTS

| | | |
|---|---|---|
| 1153578 | 9/1983 | Canada . |
| 163005 | 1/1995 | Japan . |

OTHER PUBLICATIONS

V. Abetz et al. Rheol.Acta 29:11–15 (1990), Two–color Rotary Modulated Flow Birefringence.
R.D.L. Marsh et al. Journal of Thermal Analysis, 45 (1995), 891.
K. Hongladarom et al. Macromolecules 1993, 26, 785–794.
F. Beekmans et al. Macromolecules 1996 8726–8733, vol. 29.
T. Takahashi et al., Rheol Acta 35:297–302 (1996).
K. Hongladarom et al., Macromolecules 1994, 27, 483–489.

Primary Examiner—Hoa Q. Pham

[57] ABSTRACT

A system and apparatus for the measurement of absolute biaxial birefringence of plastic materials is described. The materials which must be at least partially transparent can be constituted of one or several similar or dissimilar layers. In the latter case, the birefringence of each material can be determined. The technique uses a multiwavelength white light source that provides at least two beams projected at different angles of incidence on the sample. The beams pass through first polarizers before they are incident on the sample and through second polarizers after they have passed through the sample. The beams are then directed to a detector for measuring each beam intensity or transmittance as a function of wavelength for the incident angles at different times, and are analyzed using nonlinear regressions to determine retardation. By the knowledge of the thickness of the material, the absolute biaxial birefringences are calculated for any specific wavelength. The regression procedure incorporates the material dependent optical constants for the calculations and to discriminate between different materials for multilayer samples.

23 Claims, 12 Drawing Sheets

METHOD AND APPARATUS FOR MEASUREMENT OF ABSOLUTE BIAXIAL BIREFRINGENCE IN MONOLAYER AND MULTILAYER FILMS, SHEETS AND SHAPES

FIELD OF INVENTION

The present invention relates to a method and apparatus for the determination of the absolute biaxial birefringences in monolayer and multilayer films, sheets and other shapes by way of an analysis of light transmitted through the respective sample of the material.

BACKGROUND OF THE INVENTION

The orientation of the molecular chains in polymers is known to enhance some properties of the material, such as mechanical, optical, barrier, etc. In many polymer processing operations, it is desirable to induce orientation in the material, except some specific cases where any anisotropy in the material should be avoided, such as laser discs for example. This orientation in polymers can be induced by several processes such as film blowing, film tentering, blow molding, thermoforming, compression, rolling and drawing. In order to evaluate and optimize the polymer's properties and process conditions it is of tremendous importance to know the orientational states developed in the polymer.

Several techniques can be used for off-line measurement of orientation in polymers. These techniques include birefringence, infrared and other spectroscopy (FTIR, Raman, fluorescence, NMR, and others), X-ray scattering and ultrasonic techniques. Among these, birefringence, that is the anisotropy in refractive indices of the material, is the simplest. The orientation within the material can be described by the refractive index ellipsoid (indicatrix), which is defined by the refractive indices $n_M$, $n_T$ and $n_N$ in the three axial directions known as machine, transverse and normal, which originate from the different polarizabilities in these three directions as a result of molecular chain alignment. The refractive index which is parallel to the machine direction is designated $n_M$, the one at 90° which is the transverse direction in the material plane is designated as $n_T$, and the one in the thickness direction is $n_N$.

Birefringence is defined as the difference between the different refractive $$\Delta n_{MT} = n_M - n_T$$

$$\Delta n_{MN} = n_M - n_N$$

indices:

$$\Delta n_{TN} = n_T - n_N$$

Since there are three birefringences in any material, representing the anisotropy of optical properties in three axes, the term multiaxial birefringence is used. However, in view of the fact the three birefringences are interdependent as $$\Delta n_{TN} = n_T - n_N = (n_M - n_N) - (n_M - n_T) = \Delta n_{MN} - \Delta n_{MT}$$

expressed by the equation:
and that it is a simple calculation to determine the third birefringence once the first two are determined, the term biaxial birefringence is commonly used in the art as necessary to define the optical properties of a sample.

On the other hand, when birefringence is only measured in one plane, the term uniaxial birefringence is used.

Birefringence can be determined in two ways, such as by the measurement of refractive indices and the calculation of their differences, or by the direct measurement of the optical retardation using polarimetry techniques. Measurement of refractive indices can be performed using a refractometer such as an Abbe refractometer for example. However, such a technique has several limitations, for instance samples with shapes may be awkward to fit the refractometer, there is generally a requirement for contact solvent and the technique is cumbersome and tedious. In addition, the use of a refractometer is not applicable for on-line monitoring.

On the other hand, polarimetry techniques generally use a monochromatic light source in an optical set-up that includes a polarizer and analyzer, between which the sample to be measured is placed to measure optical retardation.

U.S. Pat. No. 4,973,163 (Sakai et al.) discloses a method for measuring birefringence using a combination of a polarizer and analyzer, with a sample interposed between them. The combination is rotated relative to the sample to determine the relationship between the angle of rotation and the intensity of light transmitted through the arrangement. Using light at two wavelengths close to each other, the retardation can be determined. When at least three wavelengths are used, different retardation values are obtained for the respective wavelength. From the retardation values, the birefringence of the simple is calculated, but only $\Delta n_{NT}$ in the plane of the sample. This technique does fit allow the determination of multiaxial birefringence and produces uncertain results in highly oriented materials.

U.S. Pat. No. 5,406,371 (Sakai et al.) discloses a method for obtaining data to calculate retardation values using in combination a white light source with a polarizer and analyzer, that rotate in unison and between which the sample is placed. The system however does not provide the multi-axial birefringence of the sample.

U.S. Pat. No. 5,319,194 (Yoshizumi et al.) discloses a method for measuring birefringence employing a laser that emits two beams at different frequencies. After the beams have passed through the sample, the beams are split by frequency and directed to two analyzers that are polarization sensitive. The devise does not make multiaxial birefringence measurements.

U.S. Pat. No. 5,257,092 (Noguchi et al.) discloses a method for measuring birefringence with a wide polarized light beam that passes through the sample, then through a rotating polarizer, and falls on a video camera detector. The system however does not provide the multiaxial birefringence of the sample.

According to U.S. Pat. No. 4,909,630 (Gawrisch et al.), an interference image of a biaxially stretched film strip is generated optically. Streaks in the film strip are areas of different orientation and/or thickness which are distinguished from the streak-free areas in the interference image by different intensities. In order to generate the interference image, a light source, a diffuser screen and a polarizer are arranged on one side of the film strip and an analyzer and a filter are arranged on the other side of the film strip. A detector, such as a video camera, is connected to an image analysis and computing unit for evaluation of the interference image. This non-quantitative technique only determines the change in orientation and/or thickness, but not the values of biaxial birefringence.

U.S. Pat. No. 4,309,110 (Tumerman) discloses an apparatus and method for determining optical properties of a substance by passing a beam of linearly polarized light through the substance. The polarization vector of light is mechanically caused to rotate at a definite frequency, and the light is measured by a photodetector. The relative phase shift and/or modulation coefficient of this beam after passing through the substance is compared with a reference beam that has not passed through the substance, to effect measurement of linear and circular birefringence. This technique uses a single wavelength, and cannot measure biaxial birefringence. If applied to moderately and highly oriented films, it would be uncertain by a factor of $2\pi$. It has the mechanical disadvantage, compared to the present invention, of requiring rotating polarizers.

U.S. Pat. No. 4,521,111 (Paulson et al.) describes an apparatus for measuring the degree and direction of molecular orientation in a film as it advances from a stretching zone. The apparatus projects ultraviolet light which does not pass through the film but stimulates fluorescence that is detected by a part of the apparatus. This technique does not measure birefringence, but a parameter called $D_{ex}$, representing the extent of orientation.

In the Japanese application JP93163005, a method and instrument for measuring retardation is disclosed. Its purpose is however to measure the retardation of a high polymer film or sheet having small anisotropy on line in the manufacturing process of the film or sheet by imposing a phase plate having known retardation between a polarizing section and analyzing section and the sheet to be measured between the phase plate and the analyzing section. This technique does not apply to high anisotropies and biaxial birefringences.

Canadian Patent 1,153,578 (Pindera) teaches a method for the optical measurement in mechanics using scattered light techniques. Specifically, this method relates to optomechanical apparatus which is useful for the rapid, accurate and theoretically correct measurements of the stress-induced birefringence, and, in particular, to determine cross-sections through elastic isodynes which carry information on the normal and shear stress components. The measurements are mentioned to be simpler when the patterns of light scattering are close to the Rayleigh model of scattering. However, this procedure is not applicable to the determination of the absolute biaxial birefringence of moderately and highly oriented materials.

In the non-patent literature, some studies mention techniques for the measurement of birefringence of materials, as described below with their advantages and disadvantages.

Abetz and Fuller, Rheol. Acta, 29, 11 (1990), describe a method that solves the problem of determining the correct birefringence and orientation angle of samples having multiple orders of retardation. The approach simultaneously uses two wavelengths of light combined with modulation of the polarization vector using a high speed rotating half wave plate, which is an achromatic wave plate. The technique is demonstrated for multiple orders in retardation. However, this method does not apply to biaxially oriented materials.

R. D. L. Marsh, J. C. Duncan and S. Brister, J. Thermal Analysis, 45, 891 (1995) published a paper on the measurement of dynamic optical birefringence, in which complex birefringence, strain and stress-optical coefficients are determined simultaneously with complex mechanical properties. Both used monochromatic light with the disadvantages mentioned above.

Hongladarom and Burghardt, Macromolecules, 26, 785 (1993), and Beekmans and de Boer, Macromolecules, 29, 8726 (1996), used a spectrographic technique for the determination of orientation of liquid crystalline polymers solutions due to their high anisotropy. This technique uses a multiwavelength source but was limited to normal incidence. The calculation procedure was not rigorous, because in the first paper (1993), the wavelength dependence of birefringence was arbitrary, and in the second paper (1996) it was not taken properly into account but approximated over a short wavelength interval. The procedure does not allow determination of biaxial birefringence.

Takahashi and Fuller (Rheol. Acta, 35, 97 (1996)) and Hongladarom and Burghardt (Macromolecules, 27, 483 (1994)) described a procedure to measure the full refractive index of solutions with a monochromatic light source and an oblique incidence. The procedure and technique described does not allow measurement of absolute birefringence of highly oriented materials.

From these examples of the prior art, it is evident that, according to present knowledge, uniaxial birefringence measurement can be accomplished in a number of ways. However, the prior art does not disclose methods or apparatus capable of making on-line biaxial birefringence measurements in samples such as moderately or highly oriented, monolayer or multilayer films, sheets or shapes in order to determine the biaxial and thus multiaxial birefingence of the samples in absolute, mathematically certain terms.

SUMMARY OF THE INVENTION

It is therefore an object of this invention to provide a method and apparatus for measuring the absolute birefringence for oriented films, sheets and shapes that are transparent or translucent.

It is a further object to provide a method and an apparatus for measuring highly biaxially oriented materials, thick samples and multilayered samples of optically different materials that are at least partially transparent to light.

These and other objects are achieved in a method and apparatus which directs at least two multiwavelength linearly polarized beams of light onto the sample, each at different angles of incidence. The intensities of each of the beams of light transmitted through the sample are measured and analyzed at a plurality of different wavelengths to determine a retardation value as a function of wavelength for each light beam. The biaxial birefringence in the sample at any specific wavelength is based on the determined retardation values.

In accordance with one aspect of this invention, the apparatus includes a multiwavelength light source unit that provides two light beams and directs them onto the sample at different angles of incidence $\theta_1$ and $\theta_2$. First polarizers are disposed in the path of each one of the beams between the light source and the sample and second polarizers are disposed in the path of each one of beams transmitted through said sample. A light intensity analyzer receives the beams to determine their intensities at different wavelengths. A computer receives the data and calculates the biaxial birefringence based on the intensities of the beams at different wavelengths. The first and second polarizers could be set to polarize the beams in the same direction or to polarize the beams at a 90° difference.

Different variations in the apparatus in accordance with the present invention are possible, depending on the specific application. The two beams transmitted through the sample at the two different angles could be continuous, could alternate between the paths or again could be generated by having a beam and the sample move relative to one another. The wavelength range of the light is preferably 350 nm to 900 nm. The light intensity analyzer is adapted to receive the beams transmitted through the sample at the different angles and to measure the intensity of each beam at different wavelengths.

In accordance with another aspect of the invention, the measured light intensity data is fitted by non-linear regression techniques to the equation:

$$I = I_r + A_t \cdot \cos^2\left(\frac{\pi \cdot \Delta n_o \cdot d}{\lambda} f(\lambda)\right)$$

in order to determine the orientation birefringence constant $\Delta n_o$ at each incident angle $\theta_1$ and $\theta_2$. This data in combination with $f(\lambda)$ is used to determine biaxial birefringences $\Delta n_{NM}$ and $\Delta n_{MT}$ at any wavelength from which $\Delta n_{TN}$ is calculated.

Many other objects and aspects of the invention will be clear from the detailed description with reference to the drawings.

BRIEF DESCRIPTION OF THE DRAWINGS

The present invention together with further objects and advantages thereof will be further understood from the following description with reference to the following drawings. In the drawings, the term spectral graph denotes a graph of light transmittance vs. light wavelength.

DETAILED DESCRIPTION OF THE INVENTION

Figure 1:
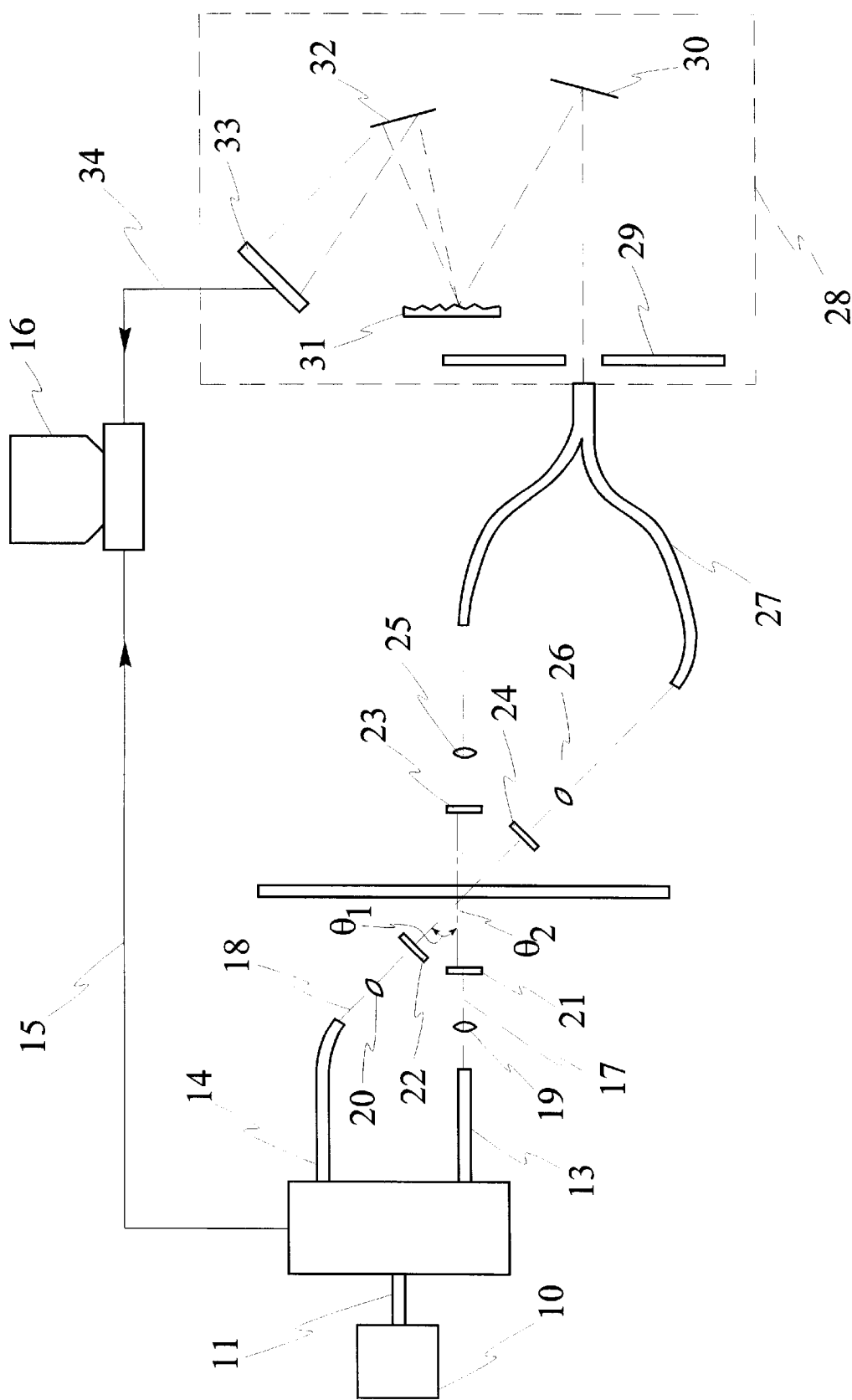
FIG. 1 is a schematic of an apparatus in accordance with the present invention wherein a light beam from a multiwavelength light source is switched between two paths that are directed through a sample.

One embodiment of the present invention is schematically represented in FIG. 1. A multiwavelength source of light 10 produces a beam of light which, through an optical fiber 11 is directed to a fiber switcher 12. Fiber switcher 12 directs the beam alternately through one and then the other of two optical fibers 13, 14 at controlled time intervals. A typical commercial light source would be the 100-watt quartz-tungsten Oriel™ QTH 6333 lamp which provides light in the approximate spectral range of 350 nm to 900 nm. The optical fiber switcher 12 may be an Oriel™ 77625 1×2 Multichannel fiber switcher. It is controlled by a TTL signal that is obtained through a line 15 from computer 16. The switching time period is adjustable, with this particular model, the minimum possible switching time is 20 ms and the minimum possible cycle time is 60 ms.

The light beam from fiber 13 is directed along a beam path 17 incident on sample 1 at an angle $\theta_1$ from an axis perpendicular to the sample while the light beam from fiber 14 is directed a long a beam path 18 incident on sample 1 at an angle $\theta_2$ from an axis perpendicular to the sample 1. It is preferable that angles $\theta_1$ and $\theta_2$ differ by at least 15°, that $\theta_2$ which is greater than $\theta_1$ be in the order of 30° to 45°. If $\theta_2$ is much greater, substantial light will be lost through reflection. It is also preferable that the beam paths 17 and 18 intersect at the sample 1, however this need not be so particularly if the sample is uniform in terms of orientation.

At the end of each of the optical fibers 13 and 14, collimating lenses 19 and 20 direct the respective light beams to polarizers 21 and 22 respectively. The polarized light beams emerging from the polarizers 21 and 22 pass through the sample 1, and into second polarizers 23 and 24 and beam-focusing lenses 25 and 26 that collect the light into a bifurcated optical fiber 27 and is fed into a detection unit 28. The detection unit 28 is a commercially available system, involving a MultiSpec™ brand spectrograph and an InstaSpec™ II brand photodiode array detector. Such a detection unit 28 contains essentially a slit 29, a mirror 30, a diffraction grating 31, a second mirror 32 and a linear photodiode array detector 33. The diffraction grating 31 disperses the light beam by wavelength, creating a spectrum that is spread across the photodiode array detector 33. The detector 33 is connected through a cable 34 to an acquisition card in a computer 16. The data are acquired in the form of a graphical spectrum of intensity or transmittance, either measurement is equally useful for the present invention since they are directly related as a function of wavelength.

It is to be noted that in this particular embodiment the fiber switcher 12 may replace the bifurcated optical fiber 27 at the other end of the beam paths 17 and 18 and be replaced by a beam splitter that would split the light beam 11 evenly between each of the paths 17 and 18. In this way, the fiber switcher 12 would switch alternately between paths 17 and 18 under the control of the computer 16 with the fiber switcher 12 output going to the detector unit 28. The disadvantage of this particular arrangement is that the intensity of the beam from the light source 10 is divided between each of the paths 17 and 18, and a higher intensity light source may be required depending on the transparency of the sample.

In most circumstances, a single reading of the intensity or transmittance through the sample at each of the angles $\theta_1$ and $\theta_2$ would be sufficient to produce the spectral graph data. However in on-line applications, the sample 1 may be a single or multi-layered film passing through the measuring apparatus at a rate of approximately 300 m per minute; it would therefore be desirable to take measurements at intervals in the order of every 2 s to continuously monitor the biaxial birefringences along the length of the moving film. As data is being collected by the computer 16, the computer 16 also computes the biaxial and/or multiaxial birefringences by non-linear regression analysis.

Figure 2:
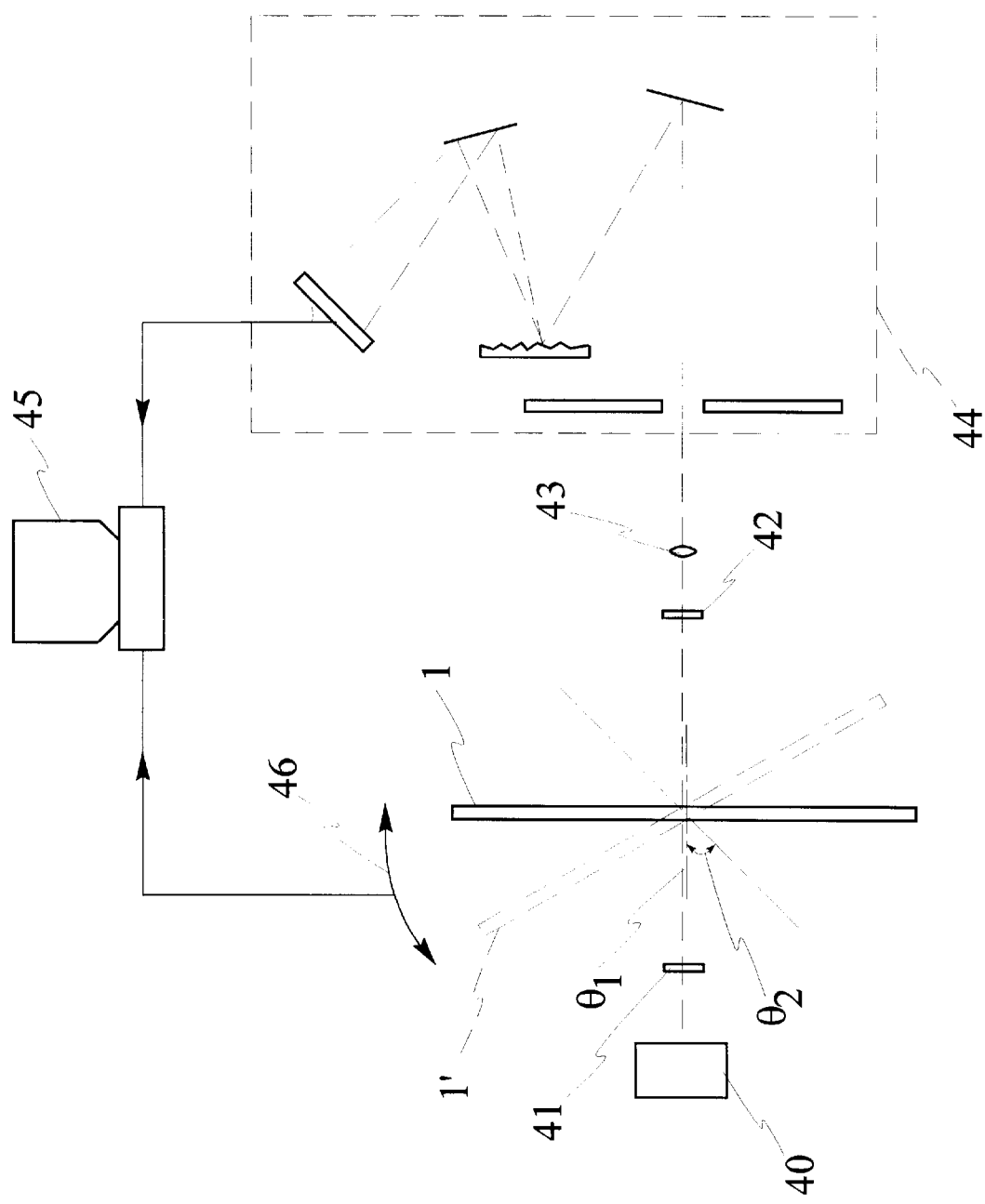
FIG. 2 is a schematic of an apparatus in accordance with the present invention wherein a light beam from a multiwavelength light source is directed through a sample along two different paths by relative motion between the light source and the sample.

A second embodiment of the present invention is illustrated in FIG. 2. In this particular embodiment, a light source 40 similar to the light source 10 in FIG. 1 generates a single multiwavelength beam and directs it to a polarizer 41 similar to polarizers 21, 22 in FIG. 1. The light beam from the polarizer 41 is incident on the sample 1 at angle $\theta_1$ where it passes through the sample 1 to a second polarizer 42, a focussing lens 43 and finally into a detection unit 44. The detection unit 44 may be identical to the unit 28 described with respect to FIG. 1. Detection unit 44 feeds data to the computer 45.

In order to obtain data similar to that collected with the apparatus in FIG. 1, the angle of incidence of the light beam on the sample 1 must be changed to take a further set of readings with an incident angle $\theta_2$. This may be accomplished in either of two ways. If sample 1 is a long moving film, then the measuring apparatus from the light source 40 to the detector unit 44 can be mounted to rotate through an angle as represented schematically by 46. With the apparatus rocking back and forth under the control of the computer 45, periodic measurements of intensity or transmittance, similar to those obtained with the apparatus in FIG. 1, can be taken at each of the incident angles $\theta_1$ and $\theta_2$. On the other hand, if the sample 1 is a fixed sample to be measured once or even scanned over a small surface area, it would be more practical to mount the sample 1 so that it could be cyclically tilted as shown in FIG. 2 to change the angle of incidence from $\theta_1$ to $\theta_2$ and back again.

Figure 3:
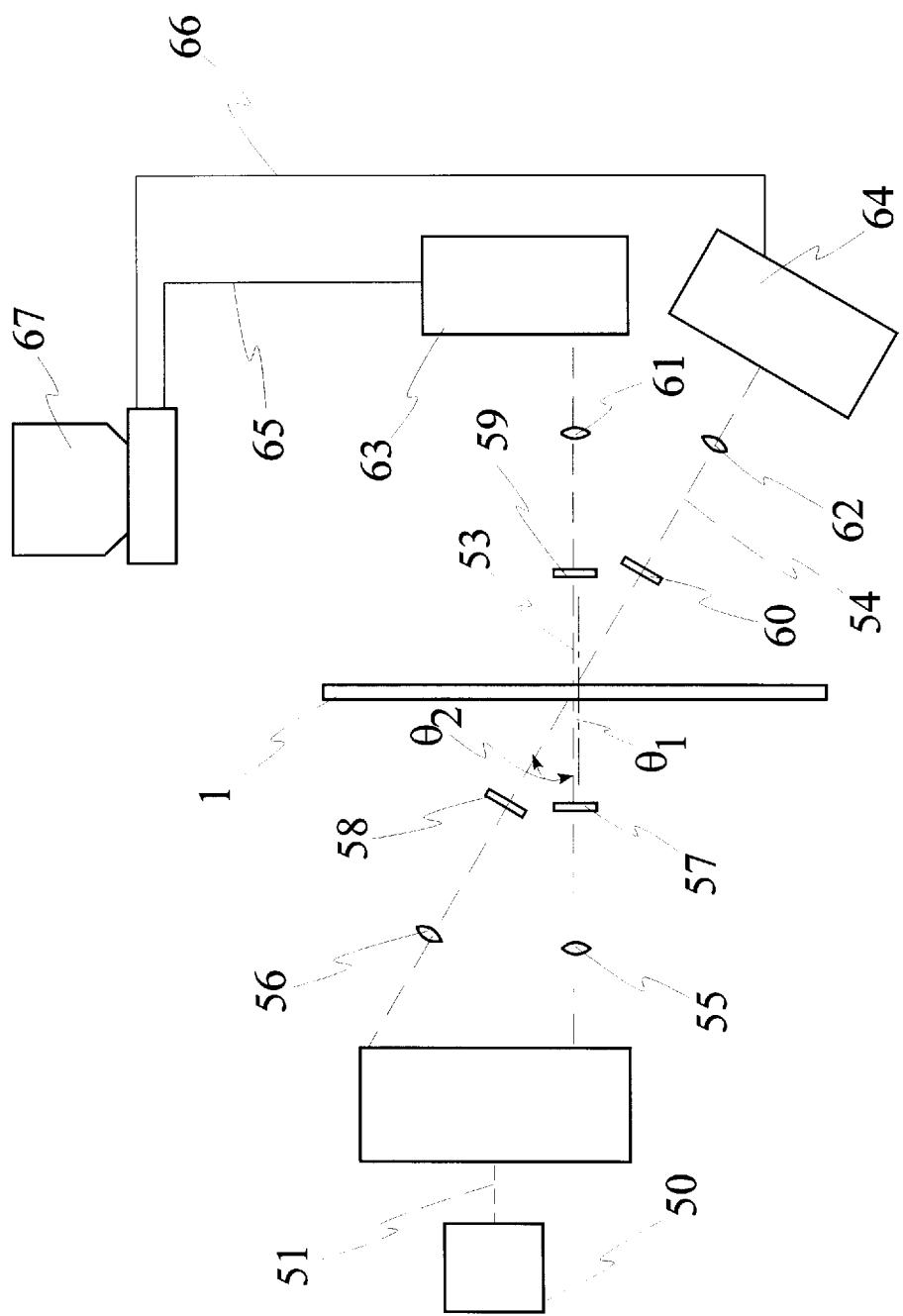
FIG. 3 is a schematic of an apparatus in accordance with the present invention wherein a light beam from a multiwavelength light source is split into two beams that are directed through a sample along two different paths.

A third embodiment of the apparatus in accordance with the present invention is illustrated with respect to FIG. 3. In this particular embodiment, a multiwavelength light source 50 similar to those previously described directs a light beam 51 into a beam splitter 52 which produces two substantially identical beams along two beam paths 53 and 54. Along each respective beam path, the beams pass through collimating lenses 55 and 56, polarizers 57 and 58, the sample 1, polarizers 59 and 60, focussing lenses 61 and 62 and then each into their respective detector units 63 and 64 of the type described with respect to FIG. 1. In this particular embodiment, continuous measurements are being taken along both paths at both incident angles $\theta_1$ to $\theta_2$. The data is fed to the computer 67 along cables 65 and 66. The computer then can sample the data at any convenient rate and compute highly accurate multiaxial birefringences since the measurements are being taken through the same spot on the sample 1 and at both angles at the same time.

Figure 4:
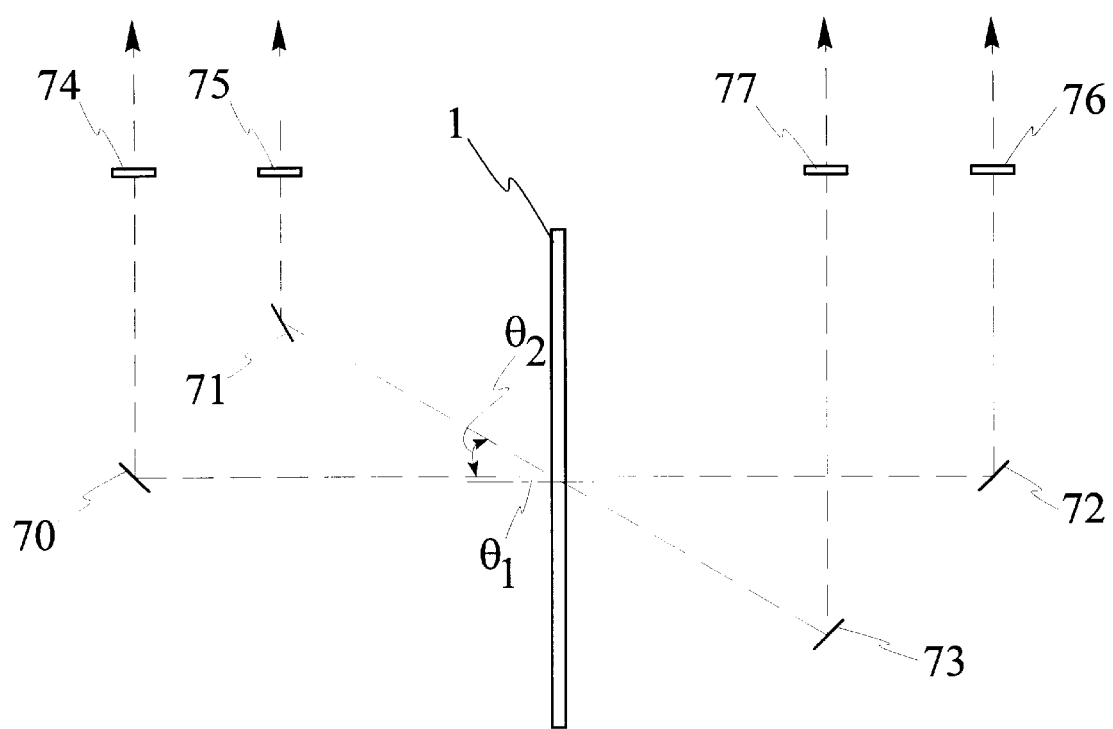
FIG. 4 is a partial schematic of an apparatus similar to FIG. 1 which includes mirrors in the light beam paths before and after the sample being measured.

FIG. 4 illustrates the use of mirrors 70 and 71 as well as 72 and 73 between the polarizers 74 and 75 as well as 76 and 77 respectively and the sample 1. The mirrors do not affect the polarized light and can therefore be used in situations where space is at a premium and the apparatus cannot be mounted in a straight line, such as in closed environments, high temperature environments, and other industrial on-line situations.

Figure 5:
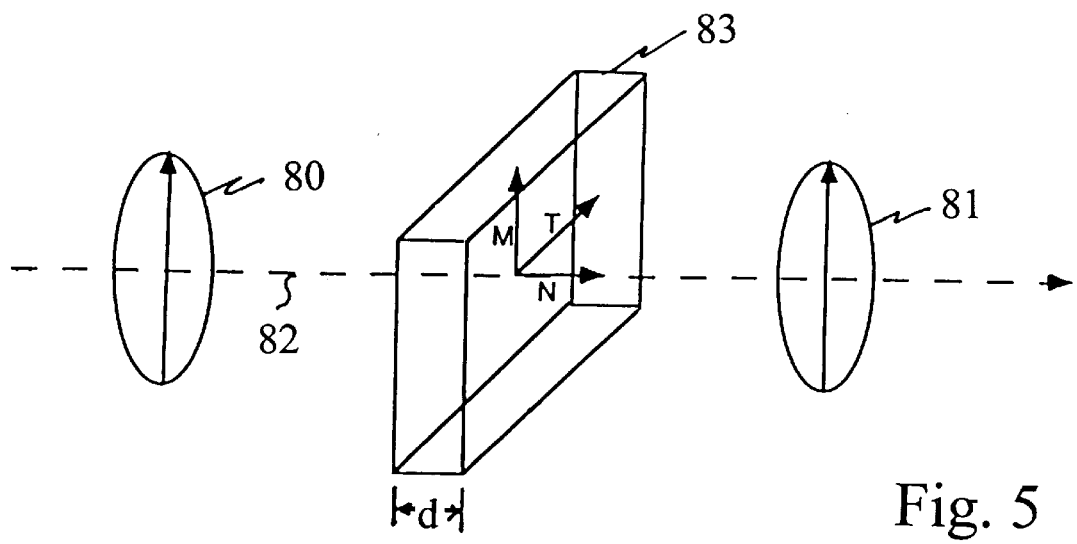
FIG. 5 is a partial schematic of an apparatus wherein the polarizers are in a parallel configuration.

As illustrated in FIG. 5, when the two polarizers 80 and 81 that are in the same light path 82 but on opposite sides of the sample 83 are oriented in the same polarization direction, and the sample 83 has a plane MT perpendicular to the light path 82, for example the machine-transverse plane it is well known in optical science that the equation for the light intensity can be written as:

$$I \propto \cos^2\left(\frac{\pi \cdot \Delta n_o \cdot d}{\lambda} f(\lambda)\right) \tag{1}$$

In this equation, I is the light intensity, $\Delta n_o$, is the orientation birefringence constant, d is the thickness of the sample, $\lambda$ is the wavelength of the light, and $f(\lambda)$ is a function of wavelength which depends on the material and expresses the variation of birefringence with wavelength. The thickness of the sample d is measured separately, and provided to the computer program by keyboard input. In most industrial applications of the invention, the thickness would already be a precisely-known parameter. The term $\Delta n_o \cdot d$ is known as the retardation, and is conventionally denoted by $\Gamma_o$, where the subscript "o" refers to a certain reference wavelength.

Figure 6:
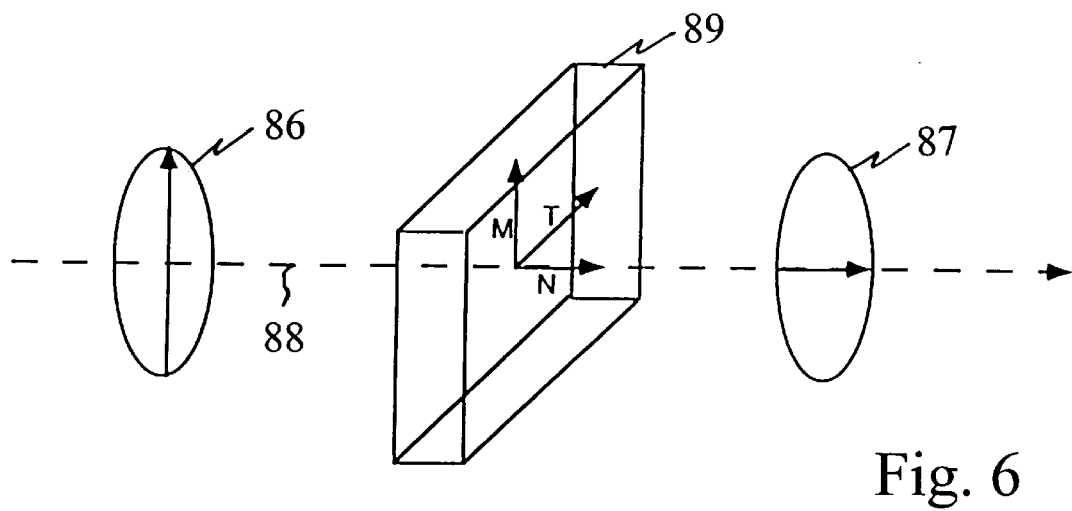
FIG. 6 is a partial schematic of an apparatus wherein the polarizers are in a crossed polarization configuration

In the situation as shown in FIG. 6 where polarizers 86 and 87 on beam path 88 passing through sample 89 are cross polarized, the cosine function in the above equation (1) should be replaced by a sine function. To reveal birefringence, the light must be polarized, but the angle of the polarization is immaterial, and is not a parameter of the equations.

It is desirable and is an object of the present invention to determine the absolute values of birefringences in a material. As noted above, the value of birefringence is, in part, determined by a calculation involving the argument of a cosine or sine function, which is a periodic function. That is, $\cos(x)=\cos(x+2\pi)=\cos(x+2n\pi)$, and similarly for the sine function. As seen, the argument of the periodic function here is the birefringence constant multiplied by the thickness of the sample, and that product would be, in general, uncertain by increments of $2\pi$. However, because multiwavelenth light is used in accordance with the present invention, only one value of a birefringence at a specific frequency is determined.

The birefringence in any plane at one wavelength $\lambda$ can be expressed as:

$$\Delta n(\lambda) = \Delta n_o \cdot f(\lambda) \tag{2}$$

Calculations of birefringence are usually made for $\lambda_0 = 589.6$ nm, corresponding to sodium light, because many other methods of determining birefringence use monochromatic light at that wavelength, and so the comparison of the present values with other methods is most relevant for this standard wavelength. However, a calculation of birefringence at any wavelength within the light used is possible with the present invention.

In real conditions, due to different optical effects (refraction, reflection, dichroism, and others), equation (1) is not rigorously satisfied, but instead takes the form:

$$I = I_r + A_t \cdot \cos^2\left(\frac{\pi \cdot \Delta n_o \cdot d}{\lambda} f(\lambda)\right) \tag{3}$$

Ir and At can be functions of wavelength, but in most cases are constants. For the $f(\lambda)$ function, different dependencies are proposed in optics textbooks and literature, but the most convenient form, which is used here, is the well-known Cauchy's formula:

$$f(\lambda) = \alpha + \frac{\beta}{\lambda^2} + \frac{\delta}{\lambda^4} + \ldots, \tag{4}$$

The $\alpha$, $\beta$ and $\delta$ constants depend on the material. In most cases, the $\alpha$ and $\beta$ terms are enough for calculations as will be evidenced in the examples below. When those terms are known in advance, as would be the case in regular on-line inspection of a known material, the terms can be provided to the computer by keyboard input, to simplify and expedite the calculation. If the terms are not known, they will be determined by non-linear regression applied to the collected data.

For a multilayer material, containing two or more significantly optically different materials, that is the dependencies of their refractive indexes as a function of wavelength are significantly different, there will be $f_a(\lambda)$, $f_b(\lambda)$, etc., each associated with a retardation in the corresponding materials. The argument of the $\cos^2$ term becomes as follows:

$$\frac{\pi}{\lambda} [\Delta n_{oa} \cdot d_a \cdot f_a(\lambda) + \Delta n_{ob} \cdot d_b \cdot f_b(\lambda) + \ldots] \quad (5)$$

Since the functions $f_a(\lambda)$, $f_b(\lambda)$ . . . can be known in terms of $\alpha_a$, $\beta_a$, $\alpha_b$, $\beta_b$, and possibly the $\delta$ terms, the regressions can be made on $I_r$, $A_t$, and the different $\Delta n_{oi}$, as will be explained in the calculations procedure below.

The same equations apply in the case of oblique incidence. The retardation obtained in this case will depend on the angle of incidence, $\theta$. The different birefringences can then be obtained from measurements at two angles, $\theta_1$ and $\theta_2$. We denote the retardation for $\theta_1$ as $\Gamma_1 = \Delta n_1 . d$, and the retardation for $\theta_2$ as $\Gamma_2 = \Delta n_2 . d$.

$$\Delta n_{MN} = \quad (6)$$

$$\frac{n}{d(\sin^2\theta_2 - \sin^2\theta_1)} [\Gamma_1 \cdot (n^2 - \sin^2\theta_1)^{1/2} - \Gamma_2 \cdot (n^2 - \sin^2\theta_2)^{1/2}]$$

Calculations lead to the following equations for the birefringences, where n designates the average refractive index:

$$\Delta n_{MT} = \frac{\Gamma_1}{n \cdot d} (n^2 - \sin^2\theta_1)^{1/2} - \frac{\sin^2\theta_1}{n^2} \Delta_{MN} \quad (7)$$

$$\Delta n_{TN} = \Delta n_{MN} - \Delta n_{MT} \quad (8)$$

Since in the intensity equation the sine or cosine functions are squared, it is not possible to know the sign of the birefringence by a single measurement. However, through the comparison of the retardation values at two different angles, this sign can be determined. In fact, following the measurement procedure mentioned above, it can be shown that if $\theta_2 > \theta_1$ for angles between 0° and 90°, the retardation $\Gamma_1$ should be greater than $\Gamma_2$ for positively birefringent materials, this indicates that the refractive index along the polymer chain is higher than in the other directions which is the case for most polymers. If $\Gamma_2$ is greater than $\Gamma_1$, it means that $\Gamma_2$ is negative and $\Gamma_1$ may be positive or negative and a measurement at another angle close to the first one is necessary to assess its sign. For negatively birefringent materials where the refractive index is higher in the plane perpendicular to the chain, such as polystyrene for example, then if $\theta_2 > \theta_1$, $\Gamma_2$ should be greater than $\Gamma_1$; if it is not the case, then the signs of the above procedure should be followed.

The data acquired as measurements on a sample can be adjusted to be in the form of intensity or transmittance, which are simply proportional to each other and are a function of wavelength. Measurements can be repeated as soon as the computer has completed the regression analysis which will depend on the speed and capacity of the computer, however 2 s cycles are acceptable in most cases. The examples of data presented below use transmittance, but the principles set out in the formulae that were written above in terms of intensity apply equally. The data are stored in the computer as they accumulate, and once they amount to a complete spectrum, non-linear regression analysis is applied to the data using methods and software that are well-known in the art. Regression analysis requires that the number of data points (coupling the transmittance to the wavelength) be much higher than the number of unknowns. The computer program compares the results of function that is initially calculated using previously known or guessed parameters, compares that with the observed function, and recalculates with revised parameters until an acceptable match is found.

The adjustable parameters, to be found by the trials of the regression program, are $I_r$, $A_t$, $\Delta n_{oi}$, $\alpha$ and $\beta$ ($\delta$ is generally negligible). In some cases, the parameters $\alpha$ and $\beta$ may be known or determined from previous measurements, and can be supplied to expedite calculations. If $\alpha$ and $\beta$ are not known, they can be determined as part of the regression analysis.

Some parameters are supplied to the calculation by keyboard input. These are:
  (a) d, the thickness of the sample, which in most industrial applications of the invention, would already be precisely known;
  (b) $\theta_1$ and $\theta_2$, the angles of incidence of the two polarized light beams;
  (c) n, the average refractive index of the sample, which is known for any material from off-line measurements using a refractometer, and industrial familiarity with the material or tabulated in handbooks.

Once the values of $I_r$, $A_t$, $\Delta n_{oi}$, $\alpha$, and $\beta$, are provided by the regression program, the birefringence can be calculated at any wavelength. To have reliable results with the regression, at least half a period of the $\cos^2$ or $\sin^2$ function should be used, so one maximum and one minimum should be observed in the experimental transmittance observations. If this half period cannot be obtained for the sample to be measured, a number of layers of the sample can be stacked with their axes in the same direction, in order to increase retardation by increasing d. The stacked sample can be measured off-line to determine the values of $\alpha$ and $\beta$ for the material and then used in the determination of birefringence of the single thickness material in the on-line industrial application.

In summary, the invention enables:
  i) Quantitative and precise measurement of absolute multiaxial birefringences,
  ii) Measurement of multiaxial birefringences of multilayer materials,
  iii) Simple, rapid and continuous monitoring of multiaxial birefringence values for quality and/or process control, as well as for the characterization of oriented plastics.

The following examples illustrate the technique and its applications.

EXAMPLE 1

Polyethylene terephthalate Film (PET)

Figure 7:
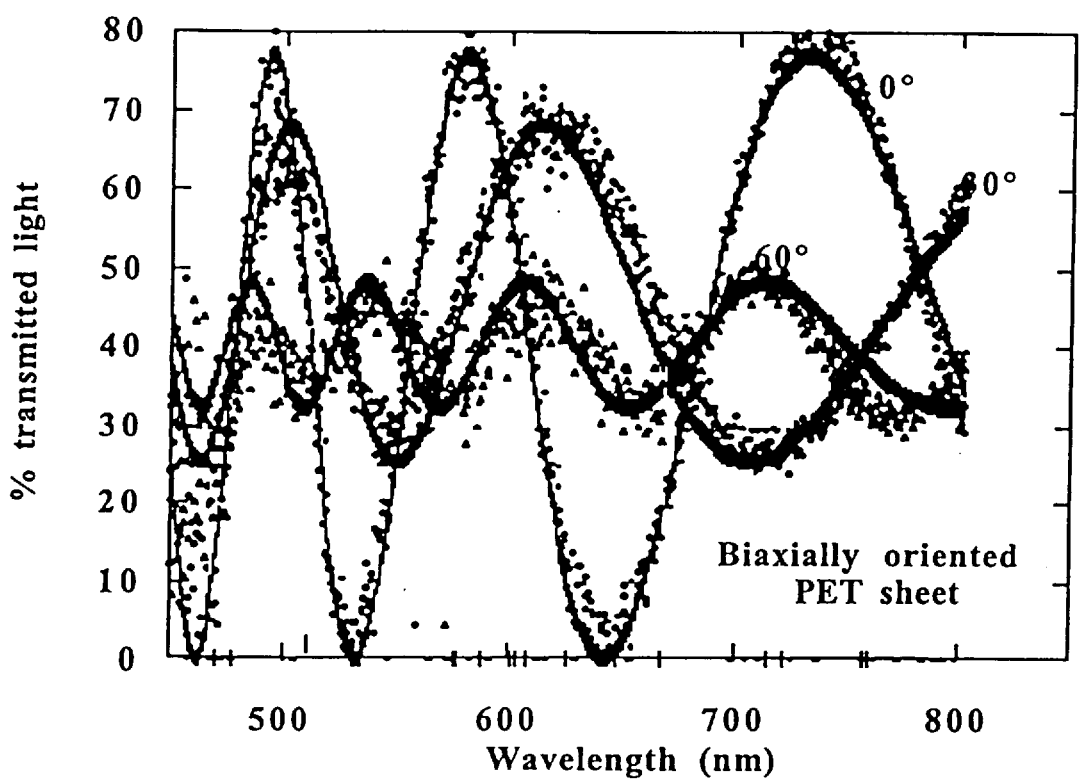
FIG. 7 is a spectral graph for a polyethylene terephthalate (PET) film.

FIG. 7 shows the results obtained for a PET film (thickness d=90 $\mu$m) obtained by the biaxial tentering orientation process. While the figure shows both the experimental (dots) and regression (vertical dashes) results at three angles, 0°, 30° and 60°. The results of the calculations are presented only for the angles 0° and 30°. The refractive index average value used for the calculations, provided by keyboard input, was 1.640. The best parameters found by regression are:

For an angle of $\theta_1=0°$:

$I_r=0$, $A_r=77$, $\Gamma_1=\Delta n_1.d=3580$ nm, $\alpha=0.800$, $\beta=1000$ nm$^2$.

For an angle of $\theta_2=30°$:

$I_r=26$, $A_r=42$, $\Gamma_2=\Delta n_2.d=2100$ mn, $\alpha=0.800$, $\beta=1000$ nm$^2$.

The retardation values are positive in this case and the regression was made assuming the same $\alpha$ and $\beta$ parameters. The values obtained for the different birefringences at a wavelength of 589 nm using the equations above are:

$\Delta n_{MT}=+0.0322$ $\Delta n_{MN}=+0.1203$ $\Delta n_{TN}=+0.0881$

Persons skilled in the art will understand, from the magnitude and the signs of these numbers, that this film is highly oriented in both the machine and the transverse directions with a lower orientation in the transverse direction.

EXAMPLE 2

Polystyrene Film (PS)

Figure 8:
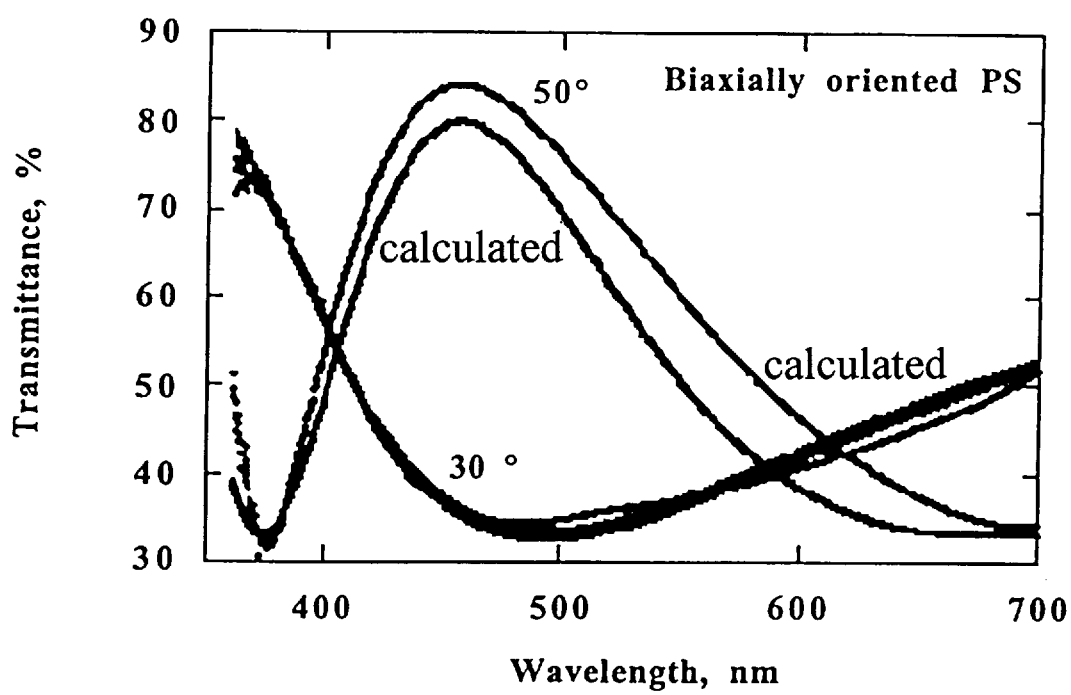
FIG. 8 is a spectral graph for a thick polystyrene (PS) film.

FIG. 8 shows the results obtained for PS film (thickness d=250 μm) obtained by the biaxial tentering orientation process. The figure shows both the experimental and regression results at two angles, 30° and 50°. The refractive index average value used for the calculations, provided by keyboard input, was 1.595. The best parameters found by regression are:

For an angle of $\theta_1=30°$:

$I_r=33$, $A_r=47$, $\Gamma_1=\Delta n_1.d=367.6$ nm, $\alpha=0.384$, $\beta=70000$ nm$^2$.

For an angle of $\theta_2=50°$:

$I_r=33$, $A_r=47$, $\Gamma_2=\Delta n_2.d=469.6$ nm, $\alpha=0.514$ and $\beta=95738$ nm$^2$.

The positive sign for $\Gamma(\lambda)=\Delta n_i.d$ is attributed to the fact that the absolute value of $\Gamma_2$ at 50° is higher than that of $\Gamma_1$ at 30° and polystyrene is a negatively birefingent material as mentioned above. In this case the regression was made on all the parameters for both angles and it was necessary in order to get acceptable agreement between calculated and measured values. The values obtained for the different birefringences at a wavelength of 589 nm using the equations above are:

$\Delta n_{MT}=0.0018$ $\Delta n_{MN}=-0.0019$ $\Delta n_{TN}=-0.0037$

Persons skilled in the art will understand, from the magnitude and the signs of these numbers, that this film is slightly oriented in the transverse and machine directions with a lower orientation in the machine direction and that uniaxial oriented polystyrene exhibits negative birefringence.

EXAMPLE 3

Polyethylene Film (PE)

Figure 9:
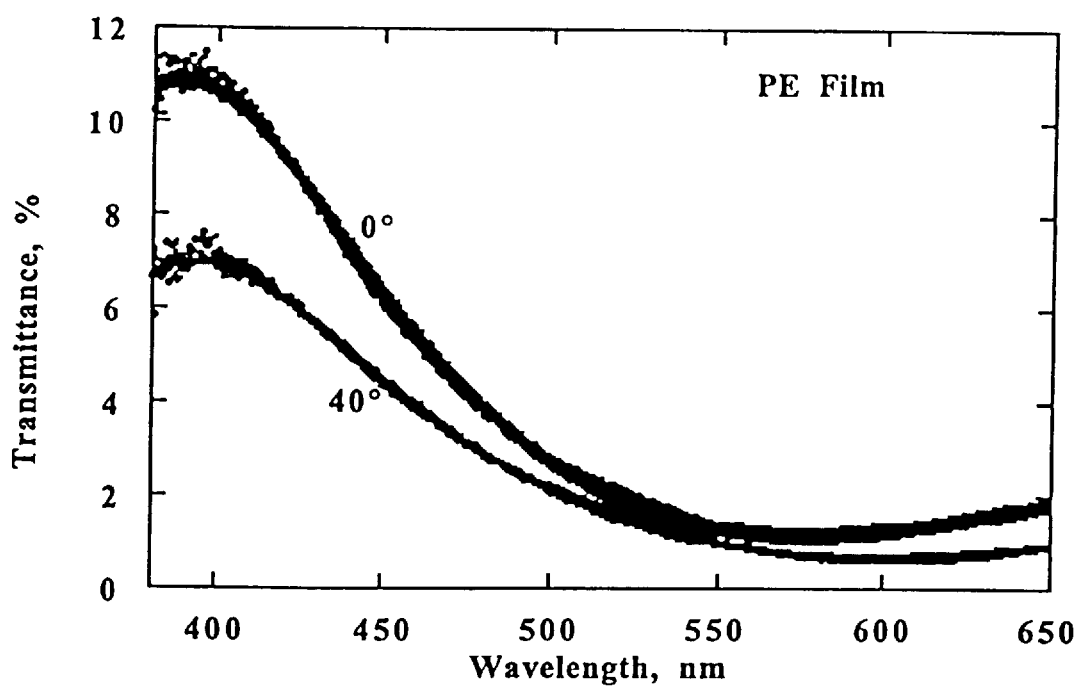
FIG. 9 is a spectral graph for a multilayer PE film, obtained according to the invention.

FIG. 9 shows the results obtained for four identical superimposed PE films (total thickness d=100 μm) obtained by film blowing. The figure shows both experimental (dots) and regression (dashes) results at two angles. The refractive index average value used for the calculations, provided by keyboard input, was 1.520. The best parameters found by regression are:

For an angle of $\theta_1=0°$:

$I_r=1.17$, $A_r=9.73$, $\Gamma_1=\Delta n_1.d=-357$ nm, $\alpha=0.570$, $\beta=78800$ nm$^2$.

For an angle of $\theta_2=40°$:

$I_r=0.72$, $A_r=6.26$, $\Gamma_2=\Delta n_2.d=-368.1$ nm, $\alpha=0.611$, $\beta=70631$ nm$^2$.

The negative sign for both $\Gamma(\lambda)=\Delta n_i.d$ is attributed to the fact that the absolute value of $\Gamma_2$ at 40° is higher than that of $\Gamma_1$ at 0° and polyethylene is a positively birefringent material as mentioned above. In this case the regression was made on all the parameters for both angles, but it was not necessary to do it on the $\alpha$ and $\beta$ parameters for the second angle and if one compares the values given by both sets of parameters in the range of wavelengths of interest (350–650), no significant differences are obtained (less than 2.5%). The values obtained for the different birefringences at a wavelength of 589 nm using the equations above are:

$\Delta n_{MT}=-0.0029$ $\Delta n_{MN}=-0.0007$ $\Delta n_{TN}=+0.0022$

Persons skilled in the art will understand, from the magnitude and the signs of these numbers, that this film is mainly oriented in the transverse direction and that the machine and normal directions are not significantly oriented. It is to be noted that this technique measures the birefringence of all of the layers as a unit since they are not substantially different.

EXAMPLE 4

Polypropylene Film (PP)

Figure 10:
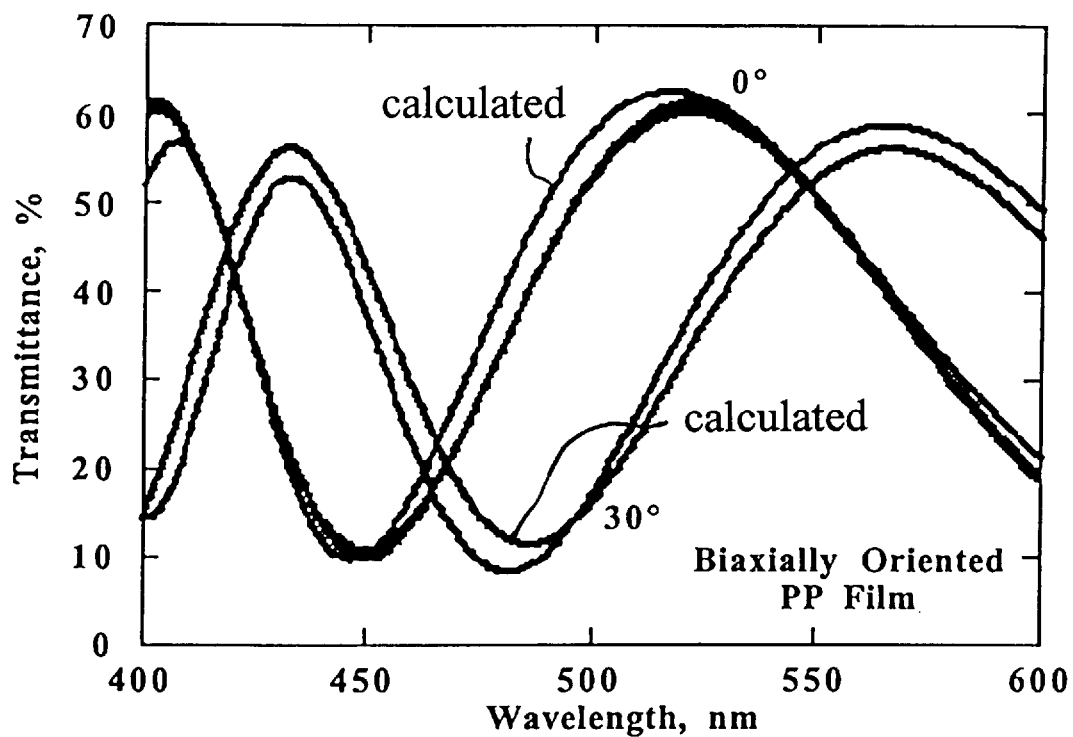
FIG. 10 is a spectral graph for a multilayer polypropelene (PP) film.

FIG. 10 shows the results obtained for four identical superimposed PP films (total thickness d=80 μm) obtained by the biaxial tentering orientation process. The figure shows both the experimental and regression results at two angles. The refractive index average value used for the calculations, provided by keyboard input, was 1.490. The best parameters found by regression are:

For an angle of $\theta_1=0°$:

$I_r=10.2$, $A_r=50.5$, $\Gamma_1=\Delta n_1.d=-1207$ nm, $\alpha=0.660$, $\beta=55346$ nm$^2$.

For an angle of $\theta_2=30°$:

$I_r=11.4$, $A_r=44.7$, $\Gamma_2=\Delta n_2.d=-1291.7$ nm, $\alpha=0.696$ and $\beta=57965$ nm$^2$.

The negative sign for $\Gamma(\lambda)=\Delta n_i.d$ is attributed to the fact that the absolute value of $\Gamma_2$ at 30° is higher than that of $\Gamma_1$ at 0° and polypropylene is a positively birefringent material as mentioned above. In this case the regression was made on all the parameters for both angles, but it was not necessary to do it on the $\alpha$ and $\beta$ parameters for the second angle and if one compares the values given by both sets of parameters in the range of wavelengths of interest (400–600), no significant differences are obtained (less than 5%). The values obtained for the different birefringences at a wavelength of 589 nm using the equations above are:

$\Delta n_{MT}=-0.012$ $\Delta n_{MN}=+0.0067$ $\Delta n_{TN}=+0.0191$

Persons skilled in the art will understand, from the magnitude and the signs of these numbers, that this film is highly oriented in the transverse direction and moderately oriented in the machine direction.

EXAMPLE 5

Uniaxality of a Polyethylene Film (PE)

Figure 11:
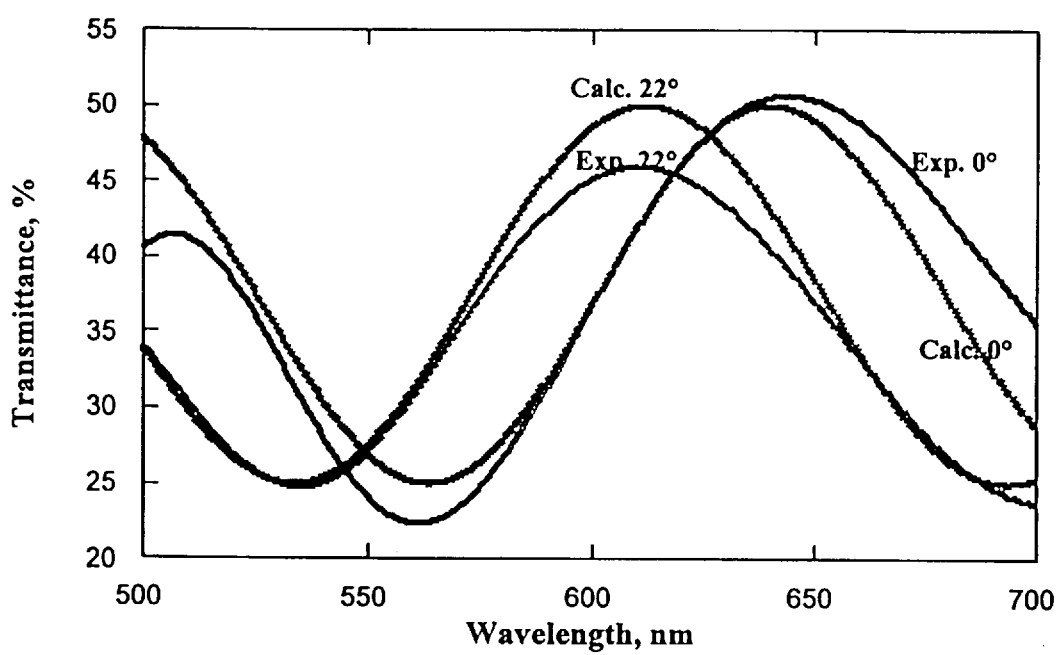
FIG. 11 is a spectral graph for a polyethylene (PE) Film.

FIG. 11 shows the results obtained for an oriented PE film for which it is desired to know if it is uniaxially or biaxially oriented. Measurements at two angles (0° and 22°) were taken and the calculations performed using the same values for the parameters $\alpha$ and $\beta$ ($\alpha=0.895$ and $\beta=-50000$). The values for $\Delta n_o.d$ obtained are as follow:

For an angle of 0°:

$\Delta n_o.d=3733$ nm

For an angle of 22°:

$\Delta n_o.d=3624$ nm

The values obtained for the different birefringences at a wavelength of 589 nm using the equations above are:

$\Delta n_{MT}=0.0593$ $\Delta n_{MN}=0.0595$ $\Delta n_{TN}=0.0002$

It is clearly seen that $\Delta n_{MT}=\Delta n_{MN}$ and that $\Delta n_{TN}$ is negligeable, which indicate that this film is uniaxially oriented.

The refractive index average value taken for these calculations was 1.520.

EXAMPLE 6

Polyester Bottle

Figure 12:
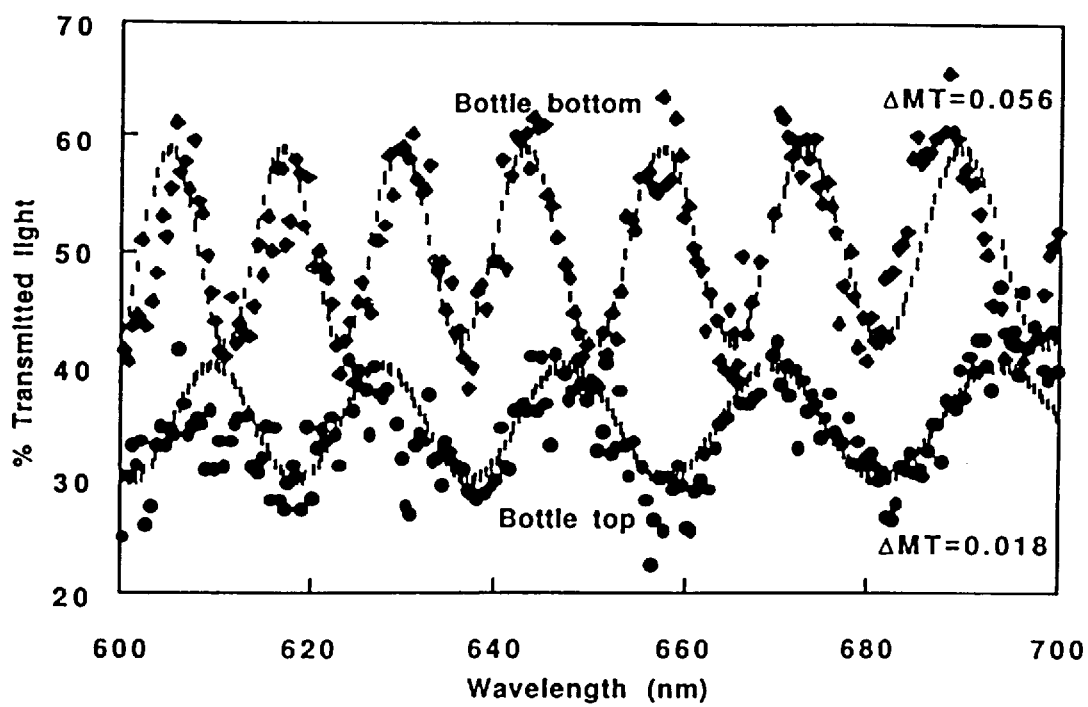
FIG. 12 is a spectral graph for a polyester blend bottle.

FIG. 12 shows the result obtained for a polyester blend bottle with the light beam directed perpendicular through the bottle at the bottom of the bottle in one case and in the other through the bottle at its top; in both cases, the beam traversed both sides of the bottle. Both experimental (dots) and calculated (vertical dashes) curves are presented. The total average thickness crossed by the light beam was 0.8 mm. An excellent agreement can be seen on the figure and the values obtained for the birefringence at a wavelength of 589 nm using the equations above were $\Delta n_{MT}=0.056$ and 0.018 for the bottom and top of the bottle respectively. This illustrates the fact that the orientation at the top and bottom of the bottle are significantly different.

EXAMPLE 7

PET/PP film

Figure 13:
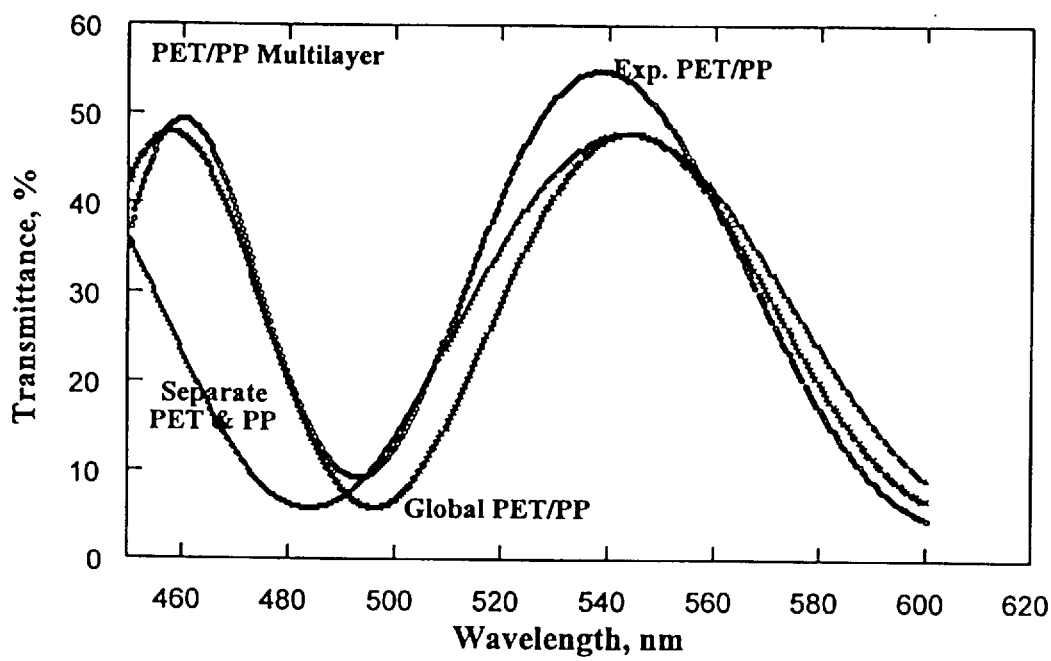
FIG. 13 is a spectral graph for a polyethylene terephthalate (PET)/polypropene (PP) multilayer film.

In this case, PET (90 $\mu$m) and PP (40 $\mu$m) films were combined and their MT birefringence measured both separately and combined, and compared. The results are presented on FIG. 13 for PET/PP. It shows the experimental results, the calculated results on a global basis (without separating the two contributions) and the calculated result for separate contributions to the function f above. The values for the parameters $\alpha$ and $\beta$ were taken as the same as those obtained for PET or PP alone (for PET $\alpha=0.800$ and $\beta=1000$ and for PP $\alpha=0.660$ and $\beta=55346$).

The values obtained for $\Delta n_o.d$ are as follow:

Global PET/PP:

$\Delta n_o.d=2587.2$ nm, $\alpha=0.735$ and $\beta=31646$ nm$^2$ $\Delta n_{MT}=0.0153$.

For separate contributions, we obtained:

For PET layer:

$\Delta n_o.d=4653.7$ nm $\Delta n_{MT}=0.0415$

For PP layer:

$\Delta n_o.d=-1204.4$ nm $\Delta n_{MT}=-0.0247$.

which, for the total orientation of the multilayer film, yields 0.0168 to be compared to 0.0153 obtained above. For the global orientation there is about 10% difference, for the separate values (they are to be compared to the values obtained for the PET and PP films alone in the previous cases) about 20% difference is noted. This may be due the parameters $\alpha$ and $\beta$ for which the exact values are not known, but this accuracy seems to be acceptable since no other means could give this kind of results as rapidly as this technique does.

Many modifications in the above described embodiments of the invention can be carried out without departing from the scope thereof and therefore the scope of the present invention is intended to be limited only by the appended claims.

We claim:

1. An apparatus for determining the biaxial birefringence of a sample at least partly transparent to light, the apparatus comprising:

multiwavelength light source means for providing at least two light beams and directing the beams at the sample at different angles of incidence;

first polarizer means disposed in the path of each one of said beams between the source and the sample;

second polarizer means disposed in the path of each one of said beams transmitted through said sample;

light intensity analyzer means disposed to determine the intensities at different wavelengths of each of said beams transmitted through said sample; and computing means for calculating the biaxial birefringence based on said intensities of the beams at different wavelengths.

2. Apparatus as claimed in claim 1 wherein the multi-wavelength light source means provides two light beams incident on the sample at angles $\theta_1$ and $\theta_2$.

3. Apparatus as claimed in claim 2 wherein the first and the second polarizer means polarize the beams in the same direction.

4. Apparatus as claimed in claim 2 wherein the second polarizers means polarize the beams at 90° to the first polarizer means.

5. Apparatus as claimed in claim 2 wherein the multi-wavelength light source means includes:
 a source for generating a multiwavelength light beam; and
 a beam switcher for controllably switching the light beam to alternately be directed onto the sample at the different angles of incidence $\theta_1$ and $\theta_2$.

6. Apparatus as claimed in claim 5 which further includes:
 beam receiving means for receiving the light beams incident on the sample at the different angles $\theta_1$ and $\theta_2$, and for directing the beams to the light intensity analyzer means.

7. Apparatus as claimed in claim 6 wherein the light intensity analyzer means consists of a first analyzer for receiving the beam incident on the sample at one angle $\theta_1$ and a second analyzer for receiving the beam incident on the sample at the other angle $\theta_2$.

8. Apparatus as claimed in claim 2 wherein the multi-wavelength light source means includes:
 a source for generating a multiwavelength light beam; and
 a beam splitter for dividing the light beam into two substantially equal beams directed onto the sample at different angles of incidence $\theta_1$ and $\theta_2$.

9. Apparatus as claimed in claim 8 which further includes:
 beam switcher means for receiving the light beams incident on the sample at the different angles $\theta_1$ and $\theta_2$, and for alternately directing the received beams to the light intensity analyzer means.

10. Apparatus as claimed in claim 2 wherein the multi-wavelength light source means includes:
 a source for generating a multiwavelength light beam; and
 means for cyclically moving the light beam source relative to the sample to direct the light beam onto the sample at different angles of incidence $\theta_1$ and $\theta_2$.

11. Apparatus as claimed in claim 2 wherein the multi-wavelength light source means includes:
 a source for generating a multiwavelength light beam; and
 means for cyclically moving the sample relative to the light beam source so that the light beam is directed onto the sample at different angles of incidence $\theta_1$ and $\theta_2$.

12. Apparatus as claimed in claim 2 which further includes first mirror means positioned between the first polarizer means and the sample to direct the polarized light beams onto the sample, and second mirror means positioned between the sample and the second polarizer means to direct the light beams to the second polarizer means.

13. A method of determining the biaxial absolute birefringence of a sample at least partly transparent to light, comprising:
 directing at least two multiwavelength linearly polarized beams of light onto the sample, each at a different angle of incidence;
 measuring the intensities of each of said beams of light transmitted through said sample at a plurality of wavelengths;
 analyzing said intensities of each of said beams at different wavelengths to determine a retardation value as a function of wavelength for each light beam; and
 determining the biaxial birefringence in the sample at any specific wavelength based on said retardation values.

14. A method as claimed in claim 13 wherein two multiwavelength linearly polarized beams of light are directed onto the sample at angles of incidence $\theta_1$ and $\theta_2$.

15. A method of determining the biaxial absolute birefringence of a sample of at least one layer of optically similar and at least partly transparent material as claimed in claim 14 wherein the measured intensity of each light beam is fitted by non-linear regression techniques to the curve defined by the equation:

$$I = I_r + A_t \cdot \cos^2\left( \frac{\pi \cdot \Delta n_o \cdot d}{\lambda} f(\lambda) \right)$$

where:
 I is the measured intensity of each beam,
 Ir and At are constants for the material,
 $\lambda$ is the wavelength of the light beam,
 d is the thickness of the sample,
 $\Delta n_o$ the orientation birefringence constant, and $$f(\lambda) = \alpha + \frac{\beta}{\lambda^2} + \frac{\delta}{\lambda^4} + \ldots$$

16. A method of determining the biaxial absolute birefringence of a sample at least partly transparent to light as claimed in claim 15 wherein the biaxial $$\Delta n_{MN} = \frac{n}{d(\sin^2\theta_2 - \sin^2\theta_1)} [\Gamma_1 \cdot (n^2 - \sin^2\theta_1)^{1/2} - \Gamma_2 \cdot (n^2 - \sin^2\theta_2)^{1/2}]$$

birefringences are determined from the equations:

$$\Delta n_{MT} = \frac{\Gamma_1}{n \cdot d} (n^2 - \sin^2\theta_1)^{1/2} - \frac{\sin^2\theta_1}{n^2} \Delta_{MN}$$

where:
 $\theta_1$ and $\theta_2$ are the angles of incidence of the beams,
 $\Gamma_1 = \Delta n_1.d$ is the retardation for $\theta_1$,
 $\Gamma_2 = \Delta n_2.d$ is the retardation for $\theta_2$, and
 n is the average refractive index of the sample.

17. A method of determining the biaxial absolute birefringence of a sample at least partly transparent to light as claimed in claim 16 wherein 350 nm <$\lambda$> 900 nM.

18. A method of determining the biaxial absolute birefringence of a sample having two or more layers a, b, ... of optically different materials and being at least partly transparent to light as claimed in claim 14 wherein the measured intensity of each light beam is fitted by non-linear regression techniques to the curve defined by the equation:

$$I = I_r + A_t \cdot \cos^2\left( \frac{\pi}{\lambda} [\Delta n_{oa} \cdot d_a \cdot f_a(\lambda) + \Delta n_{ob} \cdot d_b \cdot f_b(\lambda) + \ldots ] \right)$$

where:
 I is the measured intensity of each beam,
 Ir and At are constants for the material,
 $\lambda$ is the wavelength of the light beam,
 $d_a, d_b, \ldots$ are the thickness of the different materials in the sample, $\Delta n_{oa}, \Delta n_{ob}, \ldots$ are the orientation birefringence constants for the different materials in the sample, and $$f_a(\lambda), f_b(\lambda), \ldots = \alpha + \frac{\beta}{\lambda^2} + \frac{\delta}{\lambda^4} + \ldots$$

for the different materials in the sample.

19. A method of determining the biaxial absolute birefringence of a sample at least partly transparent to light as claimed in claim 18 wherein the biaxial birefringences are determined from the equations:

$$\Delta n_{MN} = \frac{n}{d(\sin^2\theta_2 - \sin^2\theta_1)} [\Gamma_1 \cdot (n^2 - \sin^2\theta_1)^{1/2} - \Gamma_2 \cdot (n^2 - \sin^2\theta_2)^{1/2}]$$

$$\Delta n_{MT} = \frac{\Gamma_1}{n \cdot d} (n^2 - \sin^2\theta_1)^{1/2} - \frac{\sin^2\theta_1}{n^2} \Delta_{MN}$$

where:
$\theta_1$ and $\theta_2$ are the angles of incidence of the beams,
$\Gamma_1 = \Delta n_1 \cdot d$ is the retardation for $\theta_1$,
$\Gamma_2 = \Delta n_2 \cdot d$ is the retardation for $\theta_2$, and
n is the average refractive index of the sample.

20. A method of determining the biaxial absolute birefringence of a sample at least partly transparent to light as claimed in claim 19 wherein 350 nm <λ> 900 nm.

21. A method of determining the biaxial absolute birefringence of a sample having two layers a and b of optically different materials and being at least partly transparent to light as claimed in claim 14 wherein the measured intensity of each light beam is fitted by non-linear regression techniques to the curve defined by the equation:

$$I = I_r + A_t \cdot \cos^2\left(\frac{\pi}{\lambda} [\Delta n_{oa} \cdot d_a \cdot f_a(\lambda) + \Delta n_{ob} \cdot d_b \cdot f_b(\lambda)]\right)$$

where:
I is the measured intensity of each beam,
Ir and At are constants for the material,
λ is the wavelength of the light beam,
$d_a$, $d_b$, are the thickness of the two different materials in the sample,
$\Delta n_{oa}$, $\Delta n_{ob}$ are the orientation birefringence constants for the different materials in the sample, and $$f_a(\lambda), f_b(\lambda) = \alpha + \frac{\beta}{\lambda^2} + \frac{\delta}{\lambda^4} + \ldots$$

for the different materials in the sample.

22. A method of determining the biaxial absolute birefringence of a sample at least partly transparent to light as claimed in claim 21 wherein the biaxial $$\Delta n_{MN} = \frac{n}{d(\sin^2\theta_2 - \sin^2\theta_1)} [\Gamma_1 \cdot (n^2 - \sin^2\theta_1)^{1/2} - \Gamma_2 \cdot (n^2 - \sin^2\theta_2)^{1/2}]$$

birefringences are determined from the equations:

$$\Delta n_{MT} = \frac{\Gamma_1}{n \cdot d} (n^2 - \sin^2\theta_1)^{1/2} - \frac{\sin^2\theta_1}{n^2} \Delta_{MN}$$

where:
$\theta_1$ and $\theta_2$ are the angles of incidence of the beams,
$\Gamma_1 = \Delta n_1 \cdot d$ is the retardation for $\theta_1$,
$\Gamma_2 = \Delta n_2 \cdot d$ is the retardation for $\theta_2$, and
n is the average refractive index of the sample.

23. A method of determining the biaxial absolute birefringence of a sample at least partly transparent to light as claimed in claim 22 wherein 350 nm <λ> 900 nm.

* * * * *